US00PP22024P3

(12) United States Plant Patent
Smith

(10) Patent No.: US PP22,024 P3
(45) Date of Patent: Jul. 12, 2011

(54) *PITTOSPORUM* PLANT NAMED 'CONPITTO'

(50) Latin Name: *Pittosporum tenuifolium*
Varietal Denomination: Conpitto

(75) Inventor: M. Nevin Smith, Watsonville, CA (US)

(73) Assignee: CP Delaware, Inc., Wilmington, DE (US)

( * ) Notice: Subject to any disclaimer, the term of this patent is extended or adjusted under 35 U.S.C. 154(b) by 167 days.

(21) Appl. No.: 12/461,637

(22) Filed: Aug. 19, 2009

(65) Prior Publication Data

US 2011/0047664 P1 Feb. 24, 2011

(51) Int. Cl.
*A01H 5/00* (2006.01)

(52) U.S. Cl. ..... Plt./234

(58) Field of Classification Search ..... Plt./234
See application file for complete search history.

(56) References Cited

U.S. PATENT DOCUMENTS

| | | | | | |
|---|---|---|---|---|---|
| PP4,919 | P | * | 11/1982 | Turner, Sr. | Plt./234 |
| PP6,449 | P | * | 12/1988 | Shimamoto et al. | Plt./234 |
| PP11,218 | P | * | 2/2000 | Rackley | Plt./234 |
| PP16,188 | P2 | * | 1/2006 | Taylor | Plt./234 |

* cited by examiner

*Primary Examiner* — Wendy C Haas
(74) *Attorney, Agent, or Firm* — Buchanan Ingersoll & Rooney PC

(57) ABSTRACT

A new and distinct *Pittosporum* plant is provided. Attractive green foliage with irregular light yellow margins is displayed. The growth is vigorous. An upright and columnar growth habit is displayed. The new cultivar has been found to root very easily under customary mist propagation conditions. The plant is well suited for providing attractive ornamentation when grown in the landscape.

2 Drawing Sheets

Botanical classification: *Pittosporum tenuifolium.*
Varietal denomination: cv. Conpitto.

SUMMARY OF THE INVENTION

*Pittosporum tenuifolium* is recognized to be an ornamental evergreen shrub that is believed to have originated in New Zealand. It sometimes is identified as Tawhiwki or Kohuhu.

The new *Pittosporum* plant of the present invention was discovered at a plant nursery located at Watsonville, Calif., U.S.A., while growing in a block of common *Pittosporum tenuifolium* plants (non-patented in the United States) which had been grown from seed. Accordingly, the new plant was discovered in a cultivated state within a plant nursery. The new cultivar of the present invention is believed to be a chance seedling of unknown parentage. I was primarily attracted to the single plant of the present invention in view of the distinctive appearance of its foliage. Had I not discovered and preserved this plant, it would have been lost to mankind.

The new cultivar has been carefully preserved and has been evaluated to confirm that its characteristics are reliably expressed.

It was found that the new *Pittosporum* plant of the present invention displays the following combination of characteristics:

(a) displays vigorous growth,
(b) forms attractive variegated green foliage with irregular light yellow margins,
(c) displays an upright and columnar growth habit, and
(d) is well suited for providing attractive ornamentation when grown in the landscape.

The new cultivar can be found to root very easily under customary mist propagation conditions.

The new cultivar has been grown in U.S.D.A. Hardiness Zone No. 8 and above.

The new cultivar can be distinguished from common *Pittosporum tenuifolium* plants in view of its variegated leaves. Also, the new cultivar can be readily distinguished from previously known cultivars which display variegated leaves, such as 'Marjorie Channon' (unpatented) and 'Silver Queen' (unpatented) cultivars. More specifically, the margins of the leaves of the new cultivar possess light yellow coloration unlike the margins of the previously known cultivars. The leaf margins of the 'Marjorie Channon' cultivar are more cream colored and the leaf margins of the 'Silver Queen' cultivar are more white. Also, the new cultivar is more columnar than the 'Marjorie Channon' cultivar.

The new cultivar of the present invention can be grown to advantage to provide distinctive ornamentation in the landscape.

Asexual reproduction of the new cultivar by the rooting of cuttings has been carried out at Watsonville, Calif., U.S.A., and at West Grove, Pa., U.S.A. Such propagation has confirmed that the unique combination of characteristics of the new cultivar has been stably established and is well transmitted to successive generations. The new cultivar asexually reproduces in a true-to-type manner.

The new cultivar has been named 'Conpitto' and will be marketed under the PIROUETTE trademark.

BRIEF DESCRIPTION OF THE PHOTOGRAPHS

The accompanying photographs show as nearly true as it is reasonably possible to make the same in color illustrations of this character, typical plants of the new cultivar. The plants had been asexually reproduced by the rooting of cuttings.

DETAILED DESCRIPTION

Figure 1:
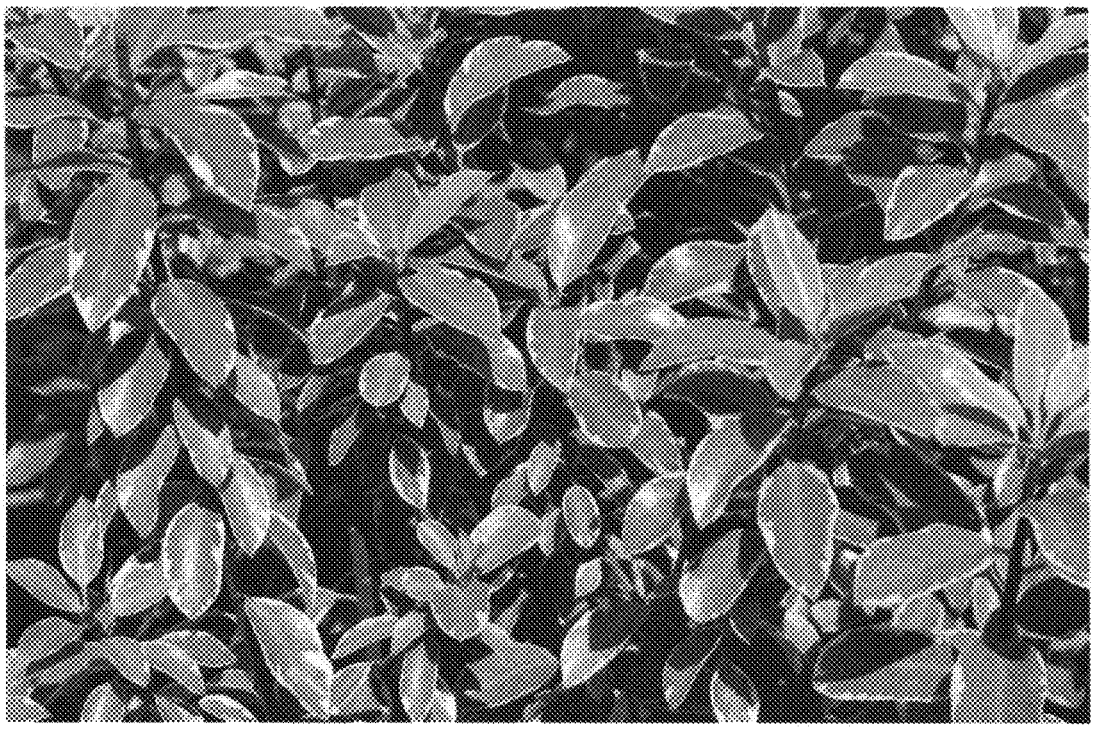
FIG. 1 shows a close view of the distinctive variegated foliage of the new cultivar wherein the irregular light yellow margins are apparent.
Figure 2:
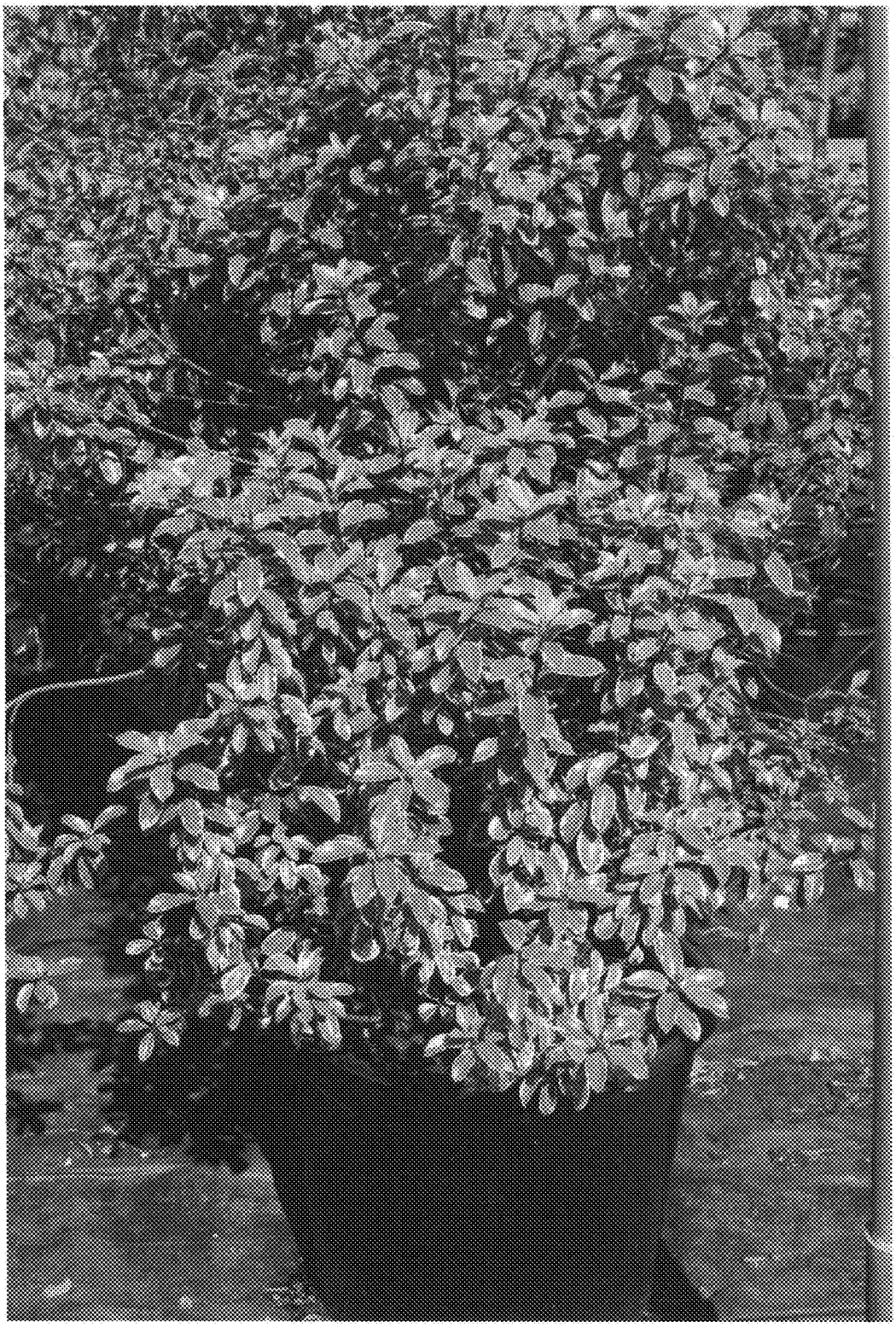
FIG. 2 shows a typical young container grown plant of the new cultivar wherein the columnar growth habit has begun to appear.

The following is a detailed description of the new cultivar of the present invention which was prepared during the spring while observing unpruned plants having an age of approximately three years, while growing in five-gallon containers outdoors near West Grove, Pa., U.S.A. Color terminology is in accordance with The R.H.S. Colour Chart (1996) of The Royal Horticultural Society, London, England, except when general color terms are used which are to be accorded their customary dictionary significance.

Type: Perennial evergreen shrub.

Plant:

*Growth habit.*—Upright and columnar, and moderately vigorous.

*Height.*—Has been observed up to approximately 1.5 m, and is estimated to have a mature height of approximately 2.5 to 4 m.

*Width*—Approximately 2.4 m.

Primary branches.—Commonly approximately 72.5 cm in length on average, and approximately 12 mm in diameter on average.

*Lateral branches.*—Commonly approximately 30 cm in length on average, and approximately 6 mm in diameter on average.

*Branch texture.*—Smooth and glabrous.

*Branching habit.*—Free, dense, and bushy.

*Roots.*—Wiry, and light brown in coloration.

*Internodes.*—Commonly approximately 0.5 to 1 cm in length.

Foliage:

*Arrangement.*—Alternate, and simple.

*Shape.*—Elliptical.

*Size.*—Commonly approximately 3 cm in length on average, and approximately 2 cm in width on average.

*Margin.*—Entire.

*Apex.*—Acute.

*Base.*—Obtuse.

*Venation.*—Pinnate.

*Texture.*—Smooth and glabrous on both surfaces.

*Color.*—Fully expanded leaves on the upper surface commonly are near Yellow-Green Group 146B at the interior and bear irregular margins of near Greyed-Yellow Group 160C, and on the under surface are near Greyed-Green Group 194B at the interior and bear irregular margins of near Greyed-Yellow Group 160C.

*Petioles.*—Smooth, glabrous, leathery, approximately 5 mm in length, approximately 1 mm in diameter, and near Green Group 138B in coloration.

Inflorescence: Flower development has not been observed during observations to date.

Development:

*Hardiness.*—U.S.D.A. Hardiness Zone No. 8 and above.

*Heat tolerance.*—Good.

*Disease resistance.*—Relatively resistant to root rot pathogens, such as *Phytophthora*, during observations to date.

The new cultivar has not been observed to date under all possible environmental conditions. Accordingly, it is possible that the phenotype may vary somewhat with variations in the environment, such as temperature, light intensity, day length, and other cultural conditions without variance of the genotype.

I claim:

1. A new and distinct *Pittosporum* plant having the following combination of characteristics:

(a) displays vigorous growth, (b) forms attractive variegated green foliage with irregular light yellow margins, (c) displays an upright and columnar growth habit, and (d) is well suited for providing attractive ornamentation when grown in the landscape;

substantially as illustrated and described.

* * * * *